(12) United States Patent
Levine et al.

(10) Patent No.: US 9,314,491 B2
(45) Date of Patent: Apr. 19, 2016

(54) TOPICAL ANTI-INFLAMMATORY COMBINATION

(71) Applicant: Izun Pharmaceuticals, Inc., New York, NY (US)

(72) Inventors: William Zev Levine, Jerusalem (IL); Aron Jay Saffer, Bet Shemesh (IL); Gabriel Nussbaum, Jerusalem (IL)

(73) Assignee: Izun Pharmaceuticals, Inc., New York, NY (US)

( * ) Notice: Subject to any disclaimer, the term of this patent is extended or adjusted under 35 U.S.C. 154(b) by 266 days.

(21) Appl. No.: 14/050,848

(22) Filed: Oct. 10, 2013

(65) Prior Publication Data

US 2014/0099389 A1    Apr. 10, 2014

Related U.S. Application Data

(63) Continuation of application No. 13/055,081, filed as application No. PCT/US2009/050661 on Jul. 15, 2009, now Pat. No. 8,771,759.

(60) Provisional application No. 61/082,613, filed on Jul. 22, 2008.

(51) Int. Cl.

| A61K 36/00 | (2006.01) |
|---|---|
| A61K 36/185 | (2006.01) |
| A61K 9/00 | (2006.01) |
| A61K 36/23 | (2006.01) |
| A61K 36/28 | (2006.01) |
| A61K 36/35 | (2006.01) |
| A61K 31/14 | (2006.01) |
| A61K 31/4425 | (2006.01) |
| A61K 47/18 | (2006.01) |

(52) U.S. Cl.
CPC ............ A61K 36/185 (2013.01); A61K 9/0014 (2013.01); A61K 31/14 (2013.01); A61K 31/4425 (2013.01); A61K 36/23 (2013.01); A61K 36/28 (2013.01); A61K 36/35 (2013.01); A61K 47/18 (2013.01)

(58) Field of Classification Search
None
See application file for complete search history.

(56) References Cited

U.S. PATENT DOCUMENTS

| 6,355,229 | B1 | 3/2002 | Adamy |
| 6,946,490 | B2 * | 9/2005 | Squires .......................... 514/643 |
| 2003/0104082 | A1 | 6/2003 | Squires |
| 2004/0151789 | A1 | 8/2004 | Levine et al. |
| 2008/0020027 | A1 | 1/2008 | Loewy et al. |

FOREIGN PATENT DOCUMENTS

| DE | 20320103 U1 | 7/2004 |
| GB | 945061 A | 12/1963 |
| JP | H-11322623 A | 11/1999 |
| JP | 2000119188 A | 4/2000 |
| JP | 2001505546 A | 4/2001 |
| JP | 2001527541 A | 12/2001 |
| WO | WO-98/11778 | 3/1998 |
| WO | WO-9811778 A1 | 3/1998 |
| WO | WO-98/42188 | 10/1998 |
| WO | WO-9842188 A1 | 10/1998 |
| WO | WO-2005034891 A2 | 4/2005 |
| WO | WO-2007144613 A1 | 12/2007 |
| WO | WO-2008011556 A2 | 1/2008 |

OTHER PUBLICATIONS

European Search Report dated Sep. 14, 2015 for Application No. 15164503.3.
Jacques et al., "Does an Increase in Membrane Unsaturated Fatty Acids Account for Tween 80 Stimulation of Glucosyltransferase Secretion by *Streptococcus salivarius*?", J Gen Microbiol, vol. 131, Issue 1, pp. 67-72, 1985.
Kawabata et al., "Effects of Selected Surfactants on Purified Glucosyltransferases From Mutans Streptococci and Cellular Adherence to Smooth Surfaces.", J Med Microbiol, vol. 38, Issue 1, pp. 54-60, 1993.
Beltrami et al., "Antinflammatory, Antimicrobial, Comedolytic Effects of a Topical Plant Complex Treatment in Acne Vulgaris: A Clinical Trial", vol. 19, Issue 1, pp. 11-20, Apr. 2001.
International Search Report Mailed on Feb. 24, 2010 PCT/US2009/050661.
Written Opinion of International Search Authority Mailed on Feb. 24, 2010 PCT/US2009/050661.
Office Action dated Nov. 24, 2010 for U.S. Appl. No. 11/780,593.
Extended European search report, Application No. 09800811.3-2107/2320920 PCT/US2009050661, 6 Pages, Sep. 29, 2012.
Pandita Narahari Rajanighantauh, 05 (p. 04-08) ( Ref.pg. no.of publication:117 ), Edn. 2nd 1998, Krishnadas Academy, Varanasi, India.†
Mohammad Najmul Ghani Khan Khazaain-al-Advia vol. III, 05 (p. 09-13) ( Ref.pg. no.of publication:973 ), (20th century AD) 1926 AD, Nadeem Yunus Printer / Sheikh Mohd Basheer & Sons, Lahore.†
Mohammad Najmul Ghani Khan Khazaain-al-Advia, vol. I, 05 (p. 14-18) ( Ref.pg. no.of publication:784 ), 1911 AD, Nadeem Yunus Printer / Sheikh Mohd Basheer & Sons, Lahore.†

* cited by examiner
† cited by third party

*Primary Examiner* — Qiuwen Mi
(74) *Attorney, Agent, or Firm* — Moser Taboada

(57) ABSTRACT

Provided, among other things, is a method of treating or ameliorating an indication of non-mucosal topical tissue comprising periodically applying to such disease affected tissue a composition comprising: an effective amount of an appropriate composition of herbal bioactive comprising active(s) of one or more of *Sambucus nigra*, *Centella asiatica* or *Echinacea purpurea*, and an effective amount of a quaternary ammonium surfactant.

18 Claims, No Drawings

TOPICAL ANTI-INFLAMMATORY COMBINATION

This application is continuation of U.S. patent application Ser. No. 13/055,081, filed 21 Feb. 2011, which is a national stage filing of PCT Application PCT/US2009/050661 (published as WO2010/011541), filed 15 Jul. 2009, which PCT application claims the priority of U.S. Prov. Application No. 61/082,613, filed 22 Jul. 2008.

The present invention relates to an anti-inflammatory topical treatment that is applied, for example, as a cream, ointment, foam, or via a patch, or via a composition-infused fabric, or the like.

Certain herbal extracts have been clinically shown to be effective in treating or ameliorating certain conditions of the mouth. Described in WO 02/094300 and U.S. Pat. No. 7,285, 295 are a number of useful combinations of herbal extracts for treating or ameliorating diseases of mucosa, and dosage forms for delivering the extracts to discrete regions of the mouth. For example, such combinations, in the delivery form described in U.S. Pat. No. 7,285,295, have achieved, in an 80 patient trial, an average of 50% pain reduction in the first ½ hour. In the same trial, average lesion reductions of 40% were achieved in 4 hours.

These types of herbal actives are not believed to have achieved substantial application as topical agents for treating topical lesions or other indications having inflammatory aspects. Similarly, quaternary ammonium surfactants, such as particularly cetylpyridinium chloride, have been used widely in oral rinses as antimicrobials. Applicants, however, have found that an oral rinse comprising an effective amount of appropriate herbal actives and an antimicrobially effective amount of a quaternary ammonium compound that is surface active is surprisingly effective in ameliorating gingivitis. The herbal actives without the quaternary ammonium compound are, in this format, marginally effective in diminishing experimental gingivitis created by subjects failing to brush for two or three weeks. Quaternary ammonium compound alone is marginally effective. The two types of agents together, however, are markedly more effective than is just the quaternary ammonium component. Against the backdrop of the effectiveness of the herbal actives alone, the marked increase in effectiveness in ameliorating gingivitis is more than additive. Given this result, Applicants conclude that other topical indications, such as those implicating mixed inflammatory and microbial etiologies, can be treated with the combination.

Provided herein are topical treatments in various compositional formats that ameliorate topical indications.

SUMMARY OF THE INVENTION

Provided, among other things, is a method of treating or ameliorating an indication of non-mucosal topical tissue comprising periodically applying to such disease affected tissue a composition comprising: an effective amount of an appropriate composition of herbal bioactive comprising active(s) of one or more of *Sambucus nigra, Centella asiatica* or *Echinacea purpurea*, and an effective amount of a quaternary ammonium surfactant. For example, the quaternary ammonium surfactant can comprise a 1-alkylpyridinium salt, where alkyl is C8-C36 (such as a cetylpyridinium salt). The composition can be applied, for example, as a film, patch. The active(s) of one or more of *Sambucus nigra, Centella asiatica* or *Echinacea purpurea* can, for example, comprise an antiinflammatory amount.

Further provided is a lotion, gel, cream, ointment or suppository comprising: an effective amount of appropriate composition of herbal bioactive comprising active(s) of one or more of *Sambucus nigra, Centella asiatica* or *Echinacea purpurea*; and an effective amount of a quaternary ammonium surfactant. The herbal bioactive can comprise, for example, active(s) of *Sambucus nigra* comprises 20 to 100% by weight of plant active solids in the composition. The herbal bioactive can comprise, for example, active(s) of a second plant extract from 1 to 50% by weight of plant active solids in the composition.

Also provided is a method of treating or ameliorating acne; contact or atopic dermatitis; impetiginized eczema; nummular eczema; endogenous chronic infectious dermatitis; stasis dermatitis; pyoderma; nuchal eczema and chronic eczematoid otitis externa; acne urticata; localized or disseminated neurodermatitis; lichen simplex chronicus; anogenital pruritus (vulvae, scroti, ani); folliculitis; bacterial dermatoses; mycotic dermatoses such as tinea (capitis, cruris, corporis, pedis, versicolor); monliasis; intertrigo; pseudomonas infections; ecthyma, candidiasis; herpes simplex lesions; dermatophytoses; staphylococcal infections (e.g., staphylococcal scalded skin syndrome); proctitis; hidradenitis suppurativa; intertrigo; rhinisitis; sinusitis; scabies; cutaneous larva migrans (hookworm); tinea (ringworm); urinary tract infections; or cutaneous penile lesions, comprising periodically applying to such disease affected tissue a composition comprising: an effective amount of an appropriate composition of herbal bioactive comprising active(s) of one or more of *Sambucus nigra, Centella asiatica* or *Echinacea purpurea*, and an effective amount of a quaternary ammonium surfactant.

Further provided, among other things, is a method of treating or ameliorating a wound comprising periodically applying to the wound a composition comprising: an effective amount of an appropriate composition of herbal bioactive comprising active(s) of one or more of *Sambucus nigra, Centella asiatica* or *Echinacea purpurea*, and an effective amount of a quaternary ammonium surfactant.

DETAILED DESCRIPTION OF THE INVENTION

1. Herbal Bioactives

Appropriate herbal bioactive compositions for use in the device include extract of *Sambucus nigra* (SN), and/or plant extracts of *Allium sativum* (AS), *Calendula officinalis* (CO), *Camellia sinensis* (CS), *Centella asiatica* (CA, also known as Gotu Kola), *Commiphora molmol* (CM), *Echinacea purpurea* (EP), *Gaultheria procumbens* (GP), *Hypericum perforatum* (HP), *Krameria triandra* (KT), *Ligusticum porteriiosha* (LP), *Matricaria recutita, Melissa officinalis, Salix alba, Thymus vulgaris, Uncaria tomentosa, Usnea barbata* or *Vaccinium myrtillus*. The herbal bioactive compositions can include, for example, *Sambucus nigra* extract in an amount from one of the lower percentages (by weight) recited in the next sentence to 20, 25, 30, 35, 40, 45, 50, 55, 60, 65, 70, 75, 80, 85, 90, 95, 96, 97, 98, 99 or 100%. These lower percentages are 10, 15, 20, 25, 30, 35, 40, 45, 50, 55, 60, 65, 70, 75, 80, 85, 90 or 95%. If a second or third herbal bioactive is present, it may be present, for example in amount from one of the lower percentages to one of the higher percentages recited in the following sentences. Lower percentages for the second or third extracts can be, for example, 0.5, 1, 2, 5, 10 or 20%. Higher percentages can be, for example, 1, 2, 5, 10, 20, 30, 40 or 50%. These ranges, and any other ranges described in this application, can include or exclude one or both endpoints.

The herbal bioactive can be a herbal extract. The term "extract" is used herein to include all of the many types of preparations containing an effective amount of active ingredients. Thus, the extracts can be produced by cold extraction techniques using a variety of different extraction solvents including, but not limited to, water, fatty solvents (such as olive oil), and alcoholic solvents (e. g. 70% ethanol). Cold extraction techniques are typically applied to softer parts of the plant such as leaves and flowers, or in cases where the desired active components of the plant are heat labile. Alternatively, hot extraction techniques, where such solvents are heated to a temperature above room temperature, can be used with the precise value of said temperature being dependent on factors such as the properties of the chosen solvent and extraction efficacy. Hot extraction techniques are more commonly applied to the harder, tougher parts of the plant, such as bark, woody branches and larger roots. In some cases, sequential extractions need to be performed in more than one solvent, and at different temperatures. Standard procedures for producing plant extracts (including hot extraction, cold extraction and other techniques) are described in many publications including "Medicinal plants: a field guide to the medicinal plants of the Land of Israel" (in Hebrew), author: N. Krispil, Har Gilo, Israel, 1986 and "Making plant medicine", author: R. Cech, pub. by Horizon Herbs, 2000.

Exemplary herbal bioactive compositions by weight percentage include:

| Plant Extract | Composition: | | | | | | | | | | | |
|---|---|---|---|---|---|---|---|---|---|---|---|---|
| | C1 | C2 | C3 | C4 | C5 | C6 | C7 | C8 | C9 | C10 | C11 | C12 |
| SN | 70 | 80 | 90 | 70 | 80 | 90 | | | | | | |
| AS | 30 | 20 | 10 | | | | | | | | | |
| CO | | | | 30 | 20 | 10 | | | | | | |
| CA | | | | | | | 30 | 20 | 10 | | | |
| CM | | | | | | | | | | 30 | 20 | 10 |
| | C13 | C14 | C15 | C16 | C17 | C18 | C19 | C20 | C21 | C22 | C23 | C24 |
| SN | 70 | 70 | 70 | 70 | 70 | 70 | 70 | 70 | 70 | 70 | 70 | 70 |
| AS | 20 | 20 | 20 | 20 | 20 | | | | | | | |
| CO | 10 | | | | | | 20 | 20 | 20 | 20 | | |
| CA | | 10 | | | | 10 | | | | 20 | 20 | 20 |
| CM | | | 10 | | | | 10 | | | 10 | | |
| EP | | | | 10 | | | | 10 | | | 10 | |
| GP | | | | | 10 | | | | 10 | | | 10 |
| | C25 | C26 | C27 | C28 | C29 | C30 | C31 | C32 | C33 | C34 | C35 | C36 |
| SN | 80 | 80 | 80 | 80 | 80 | 80 | 80 | 80 | 80 | 80 | 80 | 80 |
| AS | 10 | 10 | 10 | 10 | 10 | | | | | | | |
| CO | 10 | | | | | 10 | 10 | 10 | 10 | | | |
| CA | | 10 | | | | 10 | | | | 10 | 10 | 10 |
| CM | | | 10 | | | | 10 | | | 10 | | |
| EP | | | | 10 | | | | 10 | | | 10 | |
| GP | | | | | 10 | | | | 10 | | | 10 |
| | C37 | C38 | C39 | C40 | C41 | C42 | | C44 | C45 | C46 | C47 | C48 |
| SN | 90 | 90 | 90 | 90 | 90 | 90 | | 90 | 90 | 90 | 90 | 90 |
| AS | 10 | 9 | 8 | 7 | 6 | 5 | | 9 | 8 | 7 | 6 | 5 |
| CO | | 1 | 2 | 3 | 4 | 5 | | | | | | |
| CA | | | | | | | | 1 | 2 | 3 | 4 | 5 |
| | C49 | C50 | C51 | C52 | C53 | C54 | | C56 | C57 | C58 | C59 | C60 |
| SN | 90 | 90 | 90 | 90 | 90 | 90 | | 90 | 90 | 90 | 90 | 90 |
| AS | 10 | 9 | 8 | 7 | 6 | 5 | | 9 | 8 | 7 | 6 | 5 |
| CM | | 1 | 2 | 3 | 4 | 5 | | | | | | |
| EP | | | | | | | | 1 | 2 | 3 | 4 | 5 |
| | C61 | C62 | C63 | C64 | C65 | C66 | | | | | | |
| SN | 90 | 90 | 90 | 90 | 90 | 90 | | | | | | |
| AS | 10 | 9 | 8 | 7 | 6 | 5 | | | | | | |
| GP | | 1 | 2 | 3 | 4 | 5 | | | | | | |
| | C67 | C68 | C69 | C70 | C71 | C72 | | C74 | C75 | C76 | C77 | C78 |
| SN | 90 | 90 | 90 | 90 | 90 | 90 | | 90 | 90 | 90 | 90 | 90 |
| CO | 10 | 9 | 8 | 7 | 6 | 5 | | 9 | 8 | 7 | 6 | 5 |
| CA | | 1 | 2 | 3 | 4 | 5 | | | | | | |
| CM | | | | | | | | 1 | 2 | 3 | 4 | 5 |
| | C79 | C80 | C81 | C82 | C83 | C84 | | C86 | C87 | C88 | C89 | C90 |
| SN | 90 | 90 | 90 | 90 | 90 | 90 | | 90 | 90 | 90 | 90 | 90 |
| CM | 10 | 9 | 8 | 7 | 6 | 5 | | 9 | 8 | 7 | 6 | 5 |
| EP | | 1 | 2 | 3 | 4 | 5 | | | | | | |
| GP | | | | | | | | 1 | 2 | 3 | 4 | 5 |

-continued

| Plant Extract | Composition: | | | | | | | | | | |
|---|---|---|---|---|---|---|---|---|---|---|---|
| | C91 | C92 | C93 | C94 | C95 | C96 | C98 | C99 | C100 | C101 | C102 |
| SN | 90 | 90 | 90 | 90 | 90 | 90 | 90 | 90 | 90 | 90 | 90 |
| CA | 10 | 9 | 8 | 7 | 6 | 5 | 9 | 8 | 7 | 6 | 5 |
| CM | | 1 | 2 | 3 | 4 | 5 | | | | | |
| EP | | | | | | | 1 | 2 | 3 | 4 | 5 |
| | C103 | C104 | C105 | C106 | C107 | C108 | C110 | C111 | C112 | C113 | C114 |
| SN | 90 | 90 | 90 | 90 | 90 | 90 | 90 | 90 | 90 | 90 | 90 |
| EP | 10 | 9 | 8 | 7 | 6 | 5 | 9 | 8 | 7 | 6 | 5 |
| GP | | 1 | 2 | 3 | 4 | 5 | | | | | |
| HP | | | | | | | 1 | 2 | 3 | 4 | 5 |
| | C115 | C116 | C117 | C118 | C119 | C120 | C122 | C123 | C124 | C125 | C126 |
| SN | 90 | 90 | 90 | 90 | 90 | 90 | 90 | 90 | 90 | 90 | 90 |
| EP | 10 | 9 | 8 | 7 | 6 | 5 | 9 | 8 | 7 | 6 | 5 |
| KT | | 1 | 2 | 3 | 4 | 5 | | | | | |
| LP | | | | | | | 1 | 2 | 3 | 4 | 5 |

The above amounts provide exemplary useful amounts ±0.5% for amounts from 1-2%, ±0.5 or 1% for amounts from 3-5%, ±0.5, 1 or 2% for amounts from 6-10%, ±1, 2, 3, 4 or 5% for amounts from 70-90% (with the foregoing percentage ranges being of the total extract amount by weight).

In some embodiments, the solids from the herbal bioactive(s) typically contribute amounts to the compositions from one of the following lower endpoints or from one of the following upper endpoints. The lower endpoints are 0.01, 0.02, 0.05, 0.1, 0.2, 0.5, 1, 2, 3, 4 or 5, 10, 15, 20, 25 or 30 weight percent. The upper endpoints are 0.05, 0.1, 0.2, 0.5, 1, 2, 3, 4, 5, 6, 7, 8, 9, 10, 15, 20, 25, 30, 35, 40 or 45 weight percent.

In some embodiments the herbal bioactive can be one or more flavonoids, isoflavonoids, tocopherols, polyphenols, or similar agents often found in herbal extracts.

Flavonoids can include, for example, flavonols or flavonolols [such as, without limitation, a rutoside: rutin (quercitin 3-O-rutino-side), quercitrin (quercetin 3-O-rhamnoside), isoquercitrin (quercetin 3-O-glucoside), diosmin (diosmetin 7.beta.-rutinoside), astragalin (kaempferol 3-O-glucoside), kaempferol 3-O-rutinoside, myricitrin (or myricetin 3-O-rhamnoside), robinin (or kaempferol 3-O-robinoside 7-rhamnoside), kaempferitrin (or kaempferol 3,7-O-dirhamnoside), nobiletin, tangeretin]. Or, flavonoids can include, for example, flavones [such as, without limitation, rhoifolin (or apigenin 7-O-neohesperido-side), luteolin 7-O-glucoside, scutellarin (or scutellarein 5-O-glucoside), pectolinarin (or pectolinarigenin 7-O-rutoside), galuteolin (or luteolin 5-O-glucoside), acaciin (or acacetin 7-O-rhamnoglucoside)]. Or, flavonoids can include, for example, flavanones [such as, without limitation, liquiritin (or liquiritin 4'-O-glucoside), naringin (or naringenin 7-O-neohesperido-side), hesperidin (or hesperetin 7-O-rut-inoside), eriodictin (or eridictiol 7-O-rhamnoside)].

Isoflavonoids can include, for example: formononetin 7-O-glucoside (or ononin), afromosin 7-O-glucoside (or wistin), genistein (or genistein 7-O-glucoside), daidzin, glycitin, genistein 6-O-malonylglucoside, daidzein 6-O-malonylglucoside, genistein 6-O-acetyl-glucoside, iridin (or irigenin 7-O-glucoside), irisolone, tectoridin (or tectorigenin 7-O-glucoside) or shekanin.

If any one of these specific bioactive agents is included in the composition it can be used in an amount corresponding to the amount found in one of the above-described extracts.

2. Antimicrobial Agents

Antimicrobial quaternary ammonium surfactants can include, for example, 1-alkylpyridinium salts, where alkyl is C8-C36 (or C8-C20, or C10-C20), and wherein the carbon ring members can be substituted with up to two C1-C7 alkyl groups. For example, the composition can include cetylpyridinium chloride.

In some embodiments, the quaternary ammonium compound(s) typically contribute amounts to the compositions from one of the following lower endpoints or from one of the following upper endpoints. The lower endpoints are 0.005, 0.01, 0.02, 0.03, 0.04 and 0.05 weight percent. The upper endpoints are 5, 4, 3, 2, 1, 0.9, 0.8, 0.7, 0.6, 0.5, 0.25, 0.15, 0.14, 0.13, 0.12, 0.11, 0.10, 0.09 and 0.08 weight percent.

Such quaternary amines are traditionally used for their antiseptic action against bacteria and other microorganisms. In the treatments described herein, such antimicrobial activity may or may not be the primary mode of action for a given indication. However, an antimicrobial amount is believed to provide a good stand-in for determining how much compound to formulate.

In some part, and in some embodiments, it is believed that the therapeutic effect is due to the cleansing action of antimicrobial quaternary amines Or, in some part, and in some embodiments, it may be that the unexpectedly greater activity seen is an enhancement of the anti-inflammatory action of the herbal components by the antimicrobial quaternary amine.

4. Exemplary Topical Indications

The compositions of the invention can be used for the relief of dermatoses and similar topical indications that may be complicated by fungal, bacterial or parasitic colonization, or viral infection. Such microbial infection, if present, can be causative or secondary to the dermatosis. For wounds (including abrasions and bed sores), the compositions of the invention are believed to speed healing, and provide wound cleansing. The anti-inflammatory properties of the compositions are believed to be well suited for ameliorating pressure ulcers (bed sores).

Examples include acne; contact or atopic dermatitis; impetiginized eczema; nummular eczema; endogenous chronic infectious dermatitis; stasis dermatitis; pyoderma; nuchal eczema and chronic eczematoid otitis externa; acne urticata; localized or disseminated neurodermatitis; lichen simplex chronicus; anogenital pruritus (vulvae, scroti, ani); folliculitis; bacterial dermatoses; mycotic dermatoses such as tinea (capitis, cruris, corporis, pedis, versicolor); monliasis; intertrigo; pseudomonas infections; ecthyma, candidiasis; herpes simplex lesions; dermatophytoses; staphylococcal infections (e.g., staphylococcal scalded skin syndrome); proctitis; hidradenitis suppurativa; intertrigo; rhinisitis; sinusitis; scabies; cutaneous larva migrans (hookworm); tinea (ringworm); urinary tract infections; cutaneous penile lesions (such as balanitis zerotica obliterans, penile lichen planus, or the like); and the like.

In ameliorating acne, the compositions may reduce the growth of bacteria in the follicle (e.g., *Propionibacterium acnes* or *Staphylococcus epidermidis*), or may act to keep skin pores clear, or may act to reduce inflammation. For the purposes of this specification, acne includes all known types of acne. Types of acne include, for example, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, nodulocystic acne and acne rosacea.

The treatments of the invention are applicable to all topical surfaces. In certain embodiments, the treatments are well suited for use on non- mucosal surfaces.

Without being bound by theory, Applicants note that microbes, even symbiotic microbes, are thought to release microbial mediators of inflammation or trigger the release of cytokine. Accordingly, by reducing this stress at an affected tissue, the antimicrobial component of the compositions can have an ameliorative effect even when the indication in question does not have a strong microbial component.

5. Exemplary Formulation Formats

The compositions of the invention can be formulated in any of the many compositions used in topical or mucosal treatments. For example, the compositions can be formulated as baths or soaks, solutions, lotions, gels, creams, ointments, suppositories, dressings adapted to release the compositions, instillation solutions, foams, or the like. In certain embodiments, the compositions are applied in reservoir or adhesive patches, or in films (such as described in US2007/149902).

In certain embodiments, the combination is formulated in a lotion, gel, cream, ointment or suppository.

6. Other Dosage Forms

In certain embodiments, the composition is administered in conjunction with another administration form, such as a film, patch or mucoadhesive solid dosage form. This solid dosage form can be applied before, concurrently, or after administration of the composition. The solid forms can help deliver medicament to more severely affected, or more mechanically accessible tissue, while the composition delivers medicament elsewhere. The medicament in the solid form can be the same or different from that of the compositions of the invention. However, herbal extracts and extract mixtures as described above are usefully employed. For example, the dosage forms described in WO 02/094300 and U.S. Pat. No. 7,285,295 can be employed. Or, the film described in the an application, filed Jun. 20, 2007, titled "Anti-Inflammatory Dissolvable Film", Ser. No. 11/765,587, can be employed.

In certain embodiments, the other dosage form is adapted for systemic administration, such as by oral dosage form or by i.v. For example, the other dosage form may be a systemically administered antibiotic.

7. Antiinflamatory Agents

In certain embodiments, the composition further comprising anti-inflammatory agent(s), such as steroidal or nonsteroidal anti-inflammatory agents. Steroidal anti-inflammatory agents, include but are not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Other anti-inflammatory agents useful in the compositions include the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference can be had to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974).

Specific non-steroidal anti-inflammatory agents useful in the composition invention include, but are not limited to: 1) the oxicams, such as piroxicam, isoxicam, tenoxicam, sudoxicam, and CP-14,304; 2) the salicylates, such as aspirin, disalcid, benorylate, trilisate, safapryn, solprin, diflunisal, and fendosal; 3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; 4) the fenamates, such as mefenamic, meclofenamic, flufenamic, niflumic, and tolfenamic acids; 5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; 6) the pyrazoles, such as phenylbutazone, oxyphenbutazone, feprazone, azapropazone, and trimethazone; and mixtures of the foregoing.

Mixtures of these steroid and/or non-steroidal anti-inflammatory agents can be employed, as well as the pharmologically acceptable salts and esters of these agents. For example, etofenamate, a flufenamic acid derivative, is particularly useful for topical application.

8. Mucoadhesives

In certain embodiments polymer(s) are added to the compositions of a type, relative amount, and concentration that is mucoadhesive. The term mucoadhesive, as used herein, is a material that adheres to a mucosal tissue surface in-vivo and/or in-vitro. Such adhesion will adherently localize the dosage form onto the mucus membrane and in certain embodiments requires the application of a force of at least about 50 dynes/cm2 to separate the mucoadhesive material from the mucus membrane. Crosslinked polyacrylic acid-moiety-containing polymers and/or polysaccharide gums (e.g. chitosan) can be used to achieve such mucoadhesion.

9. Misc. Embodiments

The invention further encompasses, among other things, the following numbered embodiments:

Embodiment 1. A method of treating or ameliorating an indication of non-mucosal topical tissue comprising periodically applying to such disease affected tissue a composition comprising: an effective amount of an appropriate composition of herbal bioactive comprising active(s) of one or more of *Sambucus nigra, Centella asiatica* or *Echinacea purpurea*, and an effective amount of a quaternary ammonium surfactant.

Embodiment 2. The method of embodiment 1, wherein the quaternary ammonium surfactant comprises a 1-alkylpyridinium salt, where alkyl is C8-C36.

Embodiment 3. The method of embodiment 2, wherein the 1-alkylpyridinium salt is a cetylpyridinium salt.

Embodiment 4. The method of one of embodiments 1-3, further comprising applying to a portion of the tissue a film, patch or an adhesive solid formulation comprising appropriate composition of herbal bioactive comprising active(s) of one or more of *Sambucus nigra, Centella asiatica* or *Echinacea purpurea*.

Embodiment 5. The method of one of embodiments 1-4, wherein the composition forms a mucoadhesive coating on mucosal surfaces.

Embodiment 6. The method of one of embodiments 1-5, wherein the active(s) of one or more of *Sambucus nigra, Centella asiatica* or *Echinacea purpurea* comprise an antiinflammatory amount.

Embodiment 7. A lotion, gel, cream, ointment or suppository comprising: an effective amount of appropriate composition of herbal bioactive comprising active(s) of one or more of *Sambucus nigra, Centella asiatica* or *Echinacea purpurea*; and an effective amount of a quaternary ammonium surfactant.

Embodiment 8. The composition of embodiment 7, wherein the quaternary surfactant comprises a 1-alkylpyridinium salt, where alkyl is C8-C36.

Embodiment 9. The composition of embodiment 7, wherein the 1-alkylpyridinium salt is a cetylpyridinium salt.

Embodiment 10. The composition of one of embodiments 7-9, wherein the composition further forms a mucoadhesive coating on mucosal surfaces.

Embodiment 11. The composition of one of embodiments 7-10, wherein herbal bioactive comprising active(s) of *Sambucus nigra* comprises 20 to 100% by weight of plant active solids in the composition.

Embodiment 12. The composition of one of embodiments 11, wherein active(s) of a second plant extract from 1 to 50% by weight of plant active solids in the composition.

Embodiment 13. A method of treating or ameliorating acne; contact or atopic dermatitis; impetiginized eczema; nummular eczema; endogenous chronic infectious dermatitis; stasis dermatitis; pyoderma; nuchal eczema and chronic eczematoid otitis externa; acne urticata; localized or disseminated neurodermatitis; lichen simplex chronicus; anogenital pruritus (vulvae, scroti, ani); folliculitis; bacterial dermatoses; mycotic dermatoses such as tinea (capitis, cruris, corporis, pedis, versicolor); monliasis; intertrigo; pseudomonas infections; ecthyma, candidiasis; herpes simplex lesions; dermatophytoses; staphylococcal infections (e.g., staphylococcal scalded skin syndrome); proctitis; hidradenitis suppurativa; intertrigo; rhinisitis; sinusitis; scabies; cutaneous larva migrans (hookworm); tinea (ringworm); urinary tract infections; or cutaneous penile lesions, comprising periodically applying to such disease affected tissue a composition comprising: an effective amount of an appropriate composition of herbal bioactive comprising active(s) of one or more of *Sambucus nigra, Centella asiatica* or *Echinacea purpurea*, and an effective amount of a quaternary ammonium surfactant.

Embodiment 14. The method of embodiment 13, wherein the quaternary ammonium surfactant comprises a 1-alkylpyridinium salt, where alkyl is C8-C36.

Embodiment 15. The method of embodiment 14, wherein the 1-alkylpyridinium salt is a cetylpyridinium salt.

Embodiment 16. The method of one of embodiments 13-15, further comprising applying to a portion of the tissue a film, patch or an adhesive solid formulation comprising appropriate composition of herbal bioactive comprising active(s) of one or more of *Sambucus nigra, Centella asiatica* or *Echinacea purpurea*.

Embodiment 17. The method of one of embodiments 13-16, wherein the composition forms a mucoadhesive coating on mucosal surfaces.

Embodiment 18. The method of one of embodiments 13-17, wherein the active(s) of one or more of *Sambucus nigra, Centella asiatica* or *Echinacea purpurea* comprise an antiinflammatory amount.

Embodiment 19. A method of treating or ameliorating a wound comprising periodically applying to the wound a composition comprising: an effective amount of an appropriate composition of herbal bioactive comprising active(s) of one or more of *Sambucus nigra, Centella asiatica* or *Echinacea purpurea*, and an effective amount of a quaternary ammonium surfactant.

Embodiment 20. The method of embodiment 19, wherein the quaternary ammonium surfactant comprises a 1-alkylpyridinium salt, where alkyl is C8-C36.

Embodiment 21. The method of one of embodiments 20, wherein the 1-alkylpyridinium salt is a cetylpyridinium salt.

Embodiment 22. The method of embodiment 19, further comprising applying to a portion of the tissue a film, patch or an adhesive solid formulation comprising appropriate composition of herbal bioactive comprising active(s) of one or more of *Sambucus nigra, Centella asiatica* or *Echinacea purpurea*.

Embodiment 23. The method of one of embodiments 19-22, wherein the composition forms a mucoadhesive coating on mucosal surfaces.

Embodiment 24. The method of one of embodiments 19-23, wherein the active(s) of one or more of *Sambucus nigra, Centella asiatica* or *Echinacea purpurea* comprise an antiinflammatory amount.

Definitions

The following terms shall have, for the purposes of this application, the respective meanings set forth below.

effective amount

To treat the indications of the invention, an effective amount of a pharmaceutical compound will be recognized by clinicians but includes an amount effective to treat, reduce, alleviate, ameliorate, eliminate or prevent one or more symptoms of the disease sought to be treated or the condition sought to be avoided or treated, or to otherwise produce a clinically recognizable favorable change in the pathology of the disease or condition. Thus, an effective amount can be, for example, an amount that reduces the severity or duration of oral lesions, ulcerations, bleeding, irritation, swelling, erythema, or the like. For the present combination, it will be recognized that an effective amount is an amount that, in the combination, is effective. By way of example, if component A at concentration A1 is ineffective, component B is effective at concentration B1, and concentrations A1+B1 are more effective, then A1 is an effective amount in the combination. Or, for example if A1 and B1 are ineffective, but A1+B1 are effective, then A1 and B1 are effective amounts in the combination.

microbial infections

Microbial infections include, without limitation, bacterial, mycobacterial, fungal and viral infections.

topical

"Topical" means the any topical surface of a subject (e.g., patient), such as skin (including under the scalp), nasal, sinus, vaginal, penile, urinary or anal surfaces.

treatment

"Treatment" means the management and care of a patient for the purpose of combating a disease, disorder or condition. The term is intended to include the delaying of the progression of the disease, disorder or condition, the alleviation, amelioration or relief of symptoms and complications, and/or the cure or elimination of the disease, disorder or condition. The animal to be treated can be a mammal, in particular a human being.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of treating or ameliorating an indication of non-mucosal topical tissue that is contact or atopic dermatitis; impetiginized eczema; nummular eczema; endogenous chronic infectious dermatitis; stasis dermatitis; pyoderma; nuchal eczema; chronic eczematoid otitis externa; localized or disseminated neurodermatitis; lichen simplex chronicus; anogenital pruritus; folliculitis; bacterial dermatoses; mycotic dermatoses; moniliasis; intertrigo; pseudomonas infections; ecthyma, candidiasis; herpes simplex lesions; dermatophytoses; staphylococcal infections; proctitis; hidradenitis suppurativa; rhinitis; sinusitis; scabies; cutaneous larva migrans; tinea; urinary tract infections; or cutaneous penile lesions, comprising periodically applying to such disease affected tissue a composition comprising an effective amount of an appropriate composition of herbal extract(s) of one or more of *Sambucus nigra, Centella asiatica* or *Echinacea purpurea*, and an effective amount of a quaternary ammonium surfactant, wherein the quaternary ammonium surfactant comprises a 1-alkylpyridinium salt, where alkyl is C8-C36.

2. The method of claim 1, further comprising applying to a portion of the tissue a film, patch or an adhesive solid formulation comprising appropriate composition of herbal extract(s) of one or more of *Sambucus nigra, Centella asiatica* or *Echinacea purpurea*.

3. The method of claim 1, wherein the extract(s) of one or more of *Sambucus nigra, Centella asiatica* or *Echinacea purpurea* comprise an antiinflammatory amount.

4. The method of claim 1,
wherein *Sambucus nigra* extract is more than 50% to 90% by weight of the plant extract solids and *Centella asiatica* is 1% to less than 50% by weight of the plant extract solids, and the surfactant is a 1-alkylpyridinium salt, where alkyl is C8-C36, the surfactant present in an amount from 0.01 to 5% of the formulation by weight.

5. The method of claim 4, further comprising applying to a portion of the tissue a film, patch or an adhesive solid formulation comprising appropriate composition of herbal extract(s) of one or more of *Sambucus nigra, Centella asiatica* or *Echinacea purpurea*.

6. The method of claim 1, wherein the indication of non-mucosal topical tissue is
contact or atopic dermatitis;
impetiginized eczema;
nummular eczema;
stasis dermatitis;
nuchal eczema;
localized or disseminated neurodermatitis;
lichen simplex chronicus;
proctitis;
hidradenitis suppurativa;
sinusitis; or
cutaneous penile lesions.

7. The method of claim 6, further comprising applying to a portion of the tissue a film, patch or an adhesive solid formulation comprising appropriate composition of herbal extract(s) of one or more of *Sambucus nigra, Centella asiatica* or *Echinacea purpurea*.

8. The method of claim 6, wherein the extract(s) of one or more of *Sambucus nigra, Centella asiatica* or *Echinacea purpurea* comprise an antiinflammatory amount.

9. The method of claim 6,
wherein *Sambucus nigra* extract is more than 50% to 90% by weight of the plant extract solids and *Centella asiatica* is 1% to less than 50% by weight of the plant extract solids, and the surfactant is a 1-alkylpyridinium salt, where alkyl is C8-C36, the surfactant present in an amount from 0.01 to 5% of the formulation by weight.

10. The method of claim 9, further comprising applying to a portion of the tissue a film, patch or an adhesive solid formulation comprising appropriate composition of herbal extract(s) of one or more of *Sambucus nigra, Centella asiatica* or *Echinacea purpurea*.

11. The method of claim 1, wherein the indication of non-mucosal topical tissue is contact or atopic dermatitis.

12. The method of claim 1, wherein the indication of non-mucosal topical tissue is anogenital pruritus.

13. The method of claim 1, wherein the indication of non-mucosal topical tissue is herpes simplex lesions.

14. A method of treating or ameliorating a non-mucosal wound comprising periodically applying to the wound a composition comprising
an effective amount of an appropriate composition of herbal extract(s) of one or more of *Sambucus nigra, Centella asiatica* or *Echinacea purpurea*, and an effective amount of a quaternary ammonium surfactant that comprises a 1-alkylpyridinium salt, where alkyl is C8-C36.

15. The method of claim 14, further comprising applying to a portion of the tissue a film, patch or an adhesive solid formulation comprising appropriate composition of herbal extract(s) of one or more of *Sambucus nigra, Centella asiatica* or *Echinacea purpurea*.

16. The method of claim 14, wherein the extract(s) of one or more of *Sambucus nigra, Centella asiatica* or *Echinacea purpurea* comprise an antiinflammatory amount.

17. The method of claim 14,
   wherein *Sambucus nigra* extract is more than 50% to 90% by weight of the plant extract solids and *Centella asiatica* is 1% to less than 50% by weight of the plant extract solids, and
   the surfactant present in an amount from 0.01 to 5% of the formulation by weight.

18. The method of claim 17, further comprising applying to a portion of the tissue a film, patch or an adhesive solid formulation comprising appropriate composition of herbal extract(s) of one or more of *Sambucus nigra, Centella asiatica* or *Echinacea purpurea*.

* * * * *